United States Patent
Arnin

(10) Patent No.: US 8,163,024 B2
(45) Date of Patent: Apr. 24, 2012

(54) ADJUSTABLE SPINAL PROSTHESES

(75) Inventor: Uri Arnin, Kiryat Tivon (IL)

(73) Assignee: Premia Spine Ltd., Ramat Poleg, Netanya (IL)

( * ) Notice: Subject to any disclaimer, the term of this patent is extended or adjusted under 35 U.S.C. 154(b) by 294 days.

(21) Appl. No.: 11/224,948

(22) Filed: Sep. 14, 2005

(65) Prior Publication Data

US 2007/0073396 A1    Mar. 29, 2007

(51) Int. Cl.
*A61F 2/44* (2006.01)
(52) U.S. Cl. .................... 623/17.15; 606/246; 623/17.11
(58) Field of Classification Search .............. 606/60–61, 606/246, 266; 623/17.11–17.16
See application file for complete search history.

(56) References Cited

U.S. PATENT DOCUMENTS

| | | | | |
|---|---|---|---|---|
| 6,063,121 | A * | 5/2000 | Xavier et al. .............. | 623/17.15 |
| 6,610,093 | B1 | 8/2003 | Pisharodi | |
| 7,011,685 | B2 | 3/2006 | Arnin et al. | |
| 7,799,082 | B2 * | 9/2010 | Gordon et al. ............. | 623/17.16 |
| 7,819,900 | B2 * | 10/2010 | Parsons ......................... | 606/247 |
| 2003/0105460 | A1 * | 6/2003 | Crandall et al. ................ | 606/61 |
| 2005/0131406 | A1 | 6/2005 | Reiley et al. | |
| 2005/0182401 | A1 * | 8/2005 | Timm et al. ..................... | 606/61 |
| 2005/0240265 | A1 * | 10/2005 | Kuiper et al. .............. | 623/17.11 |
| 2005/0277930 | A1 * | 12/2005 | Parsons ........................... | 606/61 |
| 2006/0282077 | A1 * | 12/2006 | Labrom et al. .................. | 606/61 |

FOREIGN PATENT DOCUMENTS

JP    10277070    10/1998

* cited by examiner

*Primary Examiner* — Eduardo C Robert
*Assistant Examiner* — Ellen C Hammond
(74) *Attorney, Agent, or Firm* — Dekel Patent Ltd; David Klein

(57) ABSTRACT

Apparatus including a first spinal prosthetic member attachable to a first spinal structure, a second spinal prosthetic member attachable to a second spinal structure and articulating with the first spinal prosthetic member to form an articulating assembly, and pedicle screw mounting members extending outwards from the first and second spinal prosthetic members, at least one of the pedicle screw mounting members being movably attached to the first and second spinal prosthetic members such that the at least one pedicle screw mounting member has at least two different attachment orientations with respect to reference axes defined on one of the spinal prosthetic members.

10 Claims, 4 Drawing Sheets

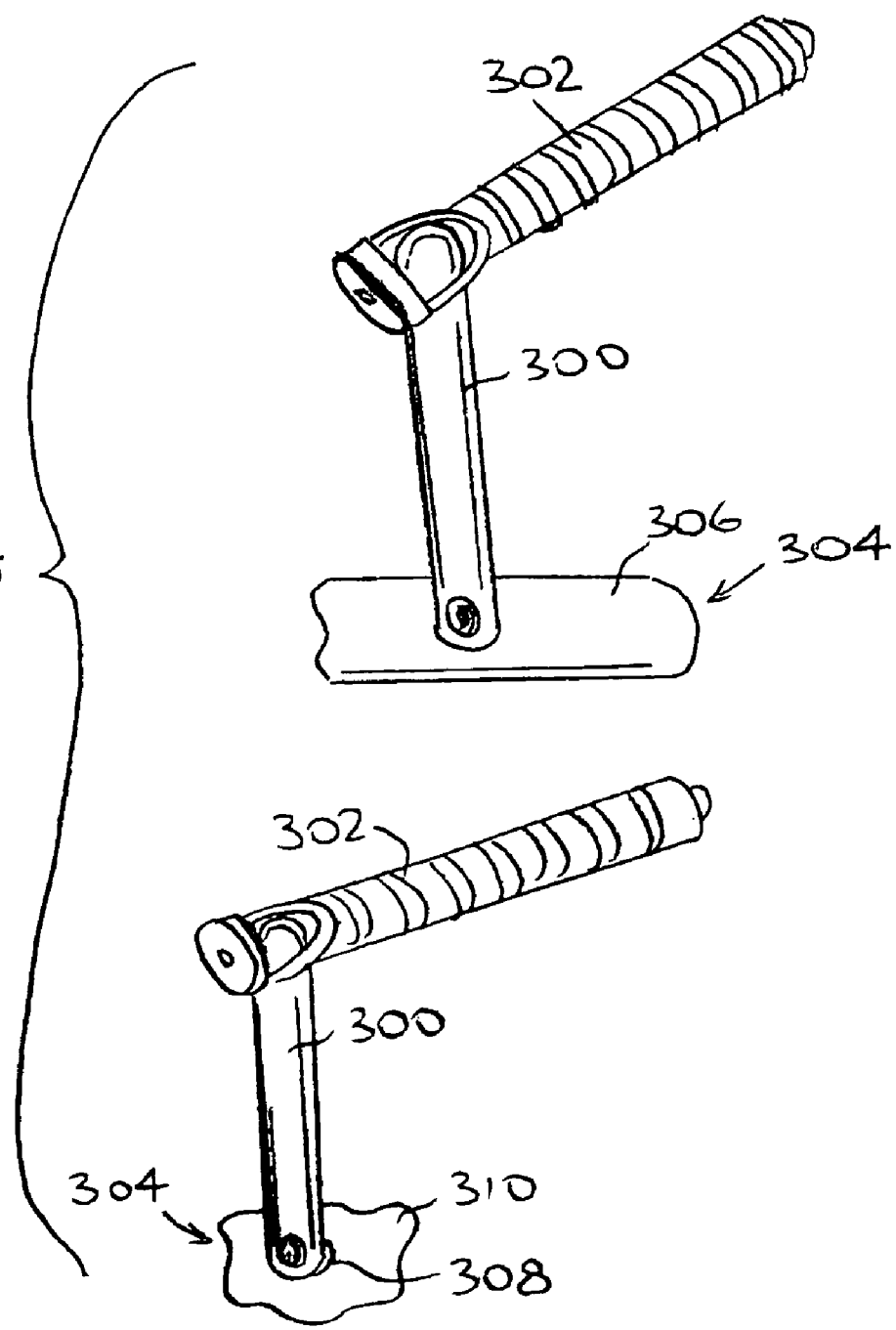

ADJUSTABLE SPINAL PROSTHESES

FIELD OF THE INVENTION

The present invention is generally related to apparatus and methods for spinal prostheses, and particularly to adjustable spinal prostheses.

BACKGROUND OF THE INVENTION

Through disease or injury, the laminae, spinous process, or articular processes of one or more vertebral bodies can become damaged, such that the vertebrae no longer articulate or properly align with each other. This can result in an undesired anatomy, loss of mobility, and pain or discomfort. For example, spinal stenosis, as well as spondylosis, spondylolisthesis, and other degenerative phenomena may cause back pain, especially lower back pain, such as in the lumbosacral (L4-S1) region. Such phenomena may be caused by a narrowing of the spinal canal by a variety of causes that result in the pinching of the spinal cord and/or nerves in the spine.

The prior art has many spinal prostheses designed to help the patient with various back problems. For example, published PCT Patent Application WO 2005/044152, assigned to the present assignee, describes a spinal prosthesis having a unitary body with three or more attachment points attachable to spinal structure. The unitary body includes a flexure assembly positioned between first and second attachment members, wherein flexure of the flexure assembly permits movement of the first attachment member relative to the second attachment member. The flexure assembly may be adapted to flex omnidirectionally. A plurality of pedicle screws (e.g., polyaxial pedicle screws with polyaxial swivel heads) may be attached to or integrally formed with the spinal prosthesis.

As another example, U.S. patent application Ser. No. 11/019,276, assigned to the present assignee, describes a spinal prosthesis that may be adjusted in-situ, such as but not limited to, being adjusted to a desired lordotic angle. The prosthesis may include a pair of spinal prosthetic members movably attached to one another with a fastening device. The fastening device has a non-tightened position which permits spatial movement of the spinal prosthetic members with respect to one another at a desired orientation, and a tightened position which fixes the first and second spinal prosthetic members at the desired orientation. The spinal prosthetic members may be pivotable with respect to one another to define an angle therebetween that corresponds to a lordotic angle between spinal structures.

SUMMARY OF THE INVENTION

The present invention seeks to provide novel spinal prostheses, as is described more in detail hereinbelow. The prostheses disclosed herein are particularly advantageous for the posterior portion of the spine, but the invention is not limited to the posterior portion of the spine. The prostheses disclosed herein may improve on, or provide features not found in, the above mentioned patent applications.

There is thus provided in accordance with an embodiment of the present invention apparatus including a first spinal prosthetic member attachable to a first spinal structure, a second spinal prosthetic member attachable to a second spinal structure and articulating with the first spinal prosthetic member to form an articulating assembly, and pedicle screw mounting members extending outwards from the first and second spinal prosthetic members, at least one of the pedicle screw mounting members being movably attached to the first and second spinal prosthetic members such that the at least one pedicle screw mounting member has at least two different attachment orientations with respect to reference axes defined on one of the spinal prosthetic members.

The spinal prosthesis can include one or more of the following features. For example, the at least one pedicle screw mounting member may be pivotable about a pivot and the at least two different attachment orientations differ from each other by an angular distance about the pivot. The at least one pedicle screw mounting member may be fixable at a plurality of angles about the pivot. At least one of the spinal prosthetic members may have more than one attachment point for attaching thereto the at least one pedicle screw mounting member, and the at least one pedicle screw mounting member may be translatable from one attachment point to another.

There is also provided in accordance with an embodiment of the present invention apparatus including a first spinal prosthetic member attachable to a first spinal structure, a second spinal prosthetic member attachable to a second spinal structure and articulating with the first spinal prosthetic member to form an articulating assembly, and a kit of pedicle screw mounting members, each pedicle screw mounting member being attachable to and adapted to extend from at least one of the first and second spinal prosthetic members, the kit including a plurality of the pedicle screw mounting members that have different attachment orientations with respect to reference axes defined on one of the spinal prosthetic members.

The different attachment orientations may differ from each other by an angular distance about a reference pivot. Alternatively or additionally, the different attachment orientations may differ from each other by a linear distance from a reference point. The kit may include pedicle screw mounting members of different lengths.

There is also provided in accordance with an embodiment of the present invention an elongate link element that may be connected between one pedicle screw and a non-pedicle-screw structure.

BRIEF DESCRIPTION OF THE DRAWINGS

In the drawings:

FIG. 5 is a simplified illustration of an elongate link element that connects between one pedicle screw and a non-pedicle-screw structure, in accordance with an embodiment of the present invention.

DETAILED DESCRIPTION OF EMBODIMENTS

Figure 1:
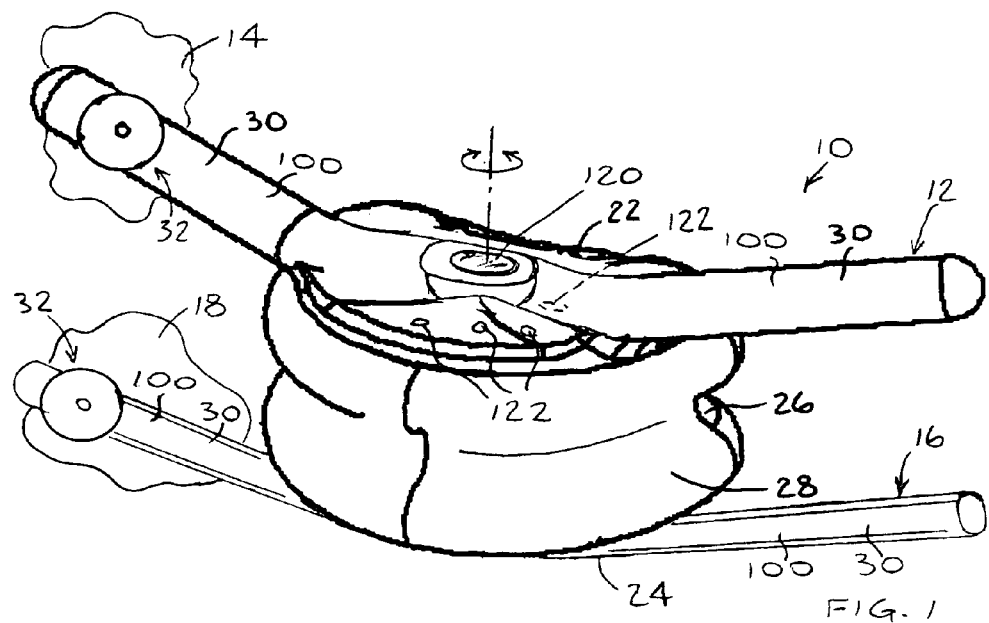
FIG. 1 is a simplified illustration of a spinal prosthesis, constructed and operative in accordance with an embodiment of the present invention.

Reference is now made to FIG. 1, which illustrates a spinal prosthesis 10, constructed and operative in accordance with an embodiment of the present invention.

The spinal prosthesis 10 may include a first spinal prosthetic member 12, which may be attached to a first spinal structure 14, such as but not limited to, a vertebra (e.g., L3). The spinal prosthesis 10 may also include a second spinal prosthetic member 16, which may be attached to a second spinal structure 18, such as but not limited to, a vertebra (e.g., L4). One non-limiting way of attaching the first and second spinal prosthetic members 12 and 16 to the first and second spinal structures 14 and 18 is described more in detail hereinbelow.

In the non-limiting illustrated embodiment, the first spinal prosthetic member 12 may include a first (e.g., upper or superior) attachment member 22 and a second (e.g., lower or inferior) attachment member 24. The attachment members 22 and 24 may be rigid or non-rigid, formed of materials including, but not limited to, a biocompatible material such as a metal, e.g., stainless steel, titanium or titanium alloy, cobalt chromium alloys, plastics or other hard, rigid materials or any combination of the above.

The first and second spinal prosthetic members 12 and 16 may articulate with each other to form an articulating assembly. For example, a flexure assembly 26 may be placed between and may be integrally formed with or attached to the first and second attachment members 22 and 24. A boot 28 may optionally be placed at least partially or fully around the first and second attachment members 22 and 24. The boot 28 may have any suitable shape or size, such as but not limited to, a ring, a stocking, an ellipsoid and other shapes. The flexure assembly 26 may be constructed of a compliant, elastomeric material including, but not limited to, polyurethane containing materials, silicone containing materials, polyethylene based elastomers, hydrogels, and polypropylene containing materials. Boot 28 may also be made of a compliant material, such as but not limited to, an elastomer (e.g., polyurethane) or cloth (woven or non-woven synthetic or natural fibers). The flexure assembly 26 may permit omnidirectional flexure of the first spinal prosthetic member 12.

Figure 3A:
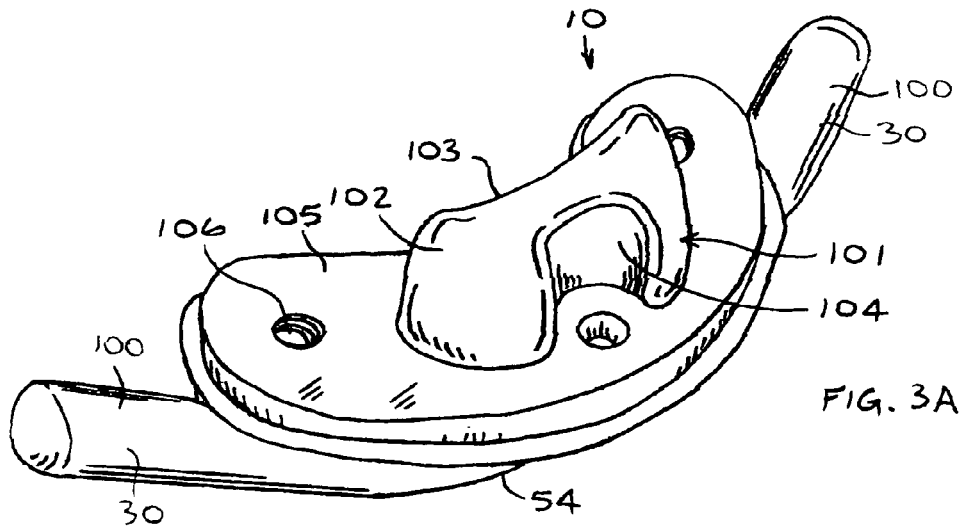
FIGS. 3A and 3B are simplified illustrations of a flexure assembly of the spinal prosthesis of FIG. 1.
Figure 3B:
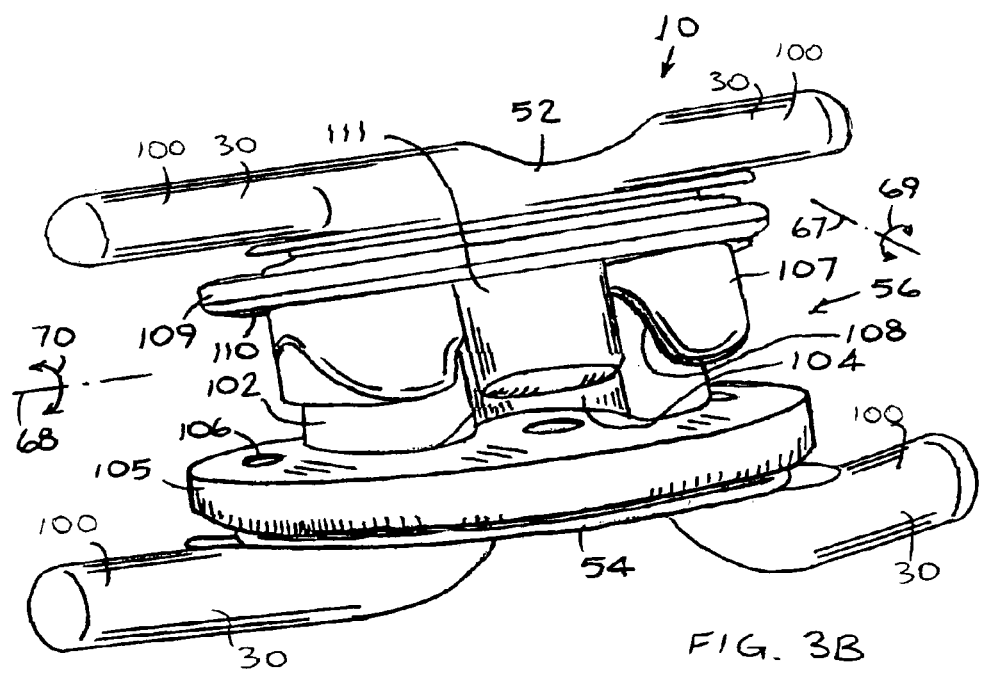

Reference is now made to FIGS. 3A and 3B. In accordance with a non-limiting embodiment of the present invention, flexure assembly 26 may include a two-part articulating assembly, as described in published PCT Patent Application WO 2005/044152, the disclosure of which is incorporated herein by reference. Flexure assembly 26 may be constructed of a first joint member 101, which may have a convex outer contour 102 with a truncated face 103. A semi-circular cutout 104 may be gouged out of the convex outer contour 102. A plate 105 may secure the first joint member 101 to a lower attachment member 54, such as with screws (not shown) that pass through mounting holes 106.

The other part of the two-part articulating assembly of flexure assembly 26 may include a second joint member 107, which may have a concave outer contour 108 that corresponds to and glides over the convex outer contour of the first joint member 101. A plate 109 may secure the second joint member 107 to an upper attachment member 52, such as with screws (not shown) that pass through mounting holes 110. A stopper 111 may be provided, either as part of the second joint member 107 or as a separate part attached to the upper attachment member 52. The stopper 111 protrudes into the semicircular cutout 104.

The flexure assembly 26 permits flexure of prosthesis 10 about two mutually orthogonal axes 67 (in the direction of arrows 69) and 68 (in the direction of arrows 70) as well as other directions for omnidirectional flexure in any degree of freedom. The stopper 111 may limit the flexure of the prosthesis and thus limit the relative movement of the attachment members 52 and 54 with respect to one another.

Figure 2:
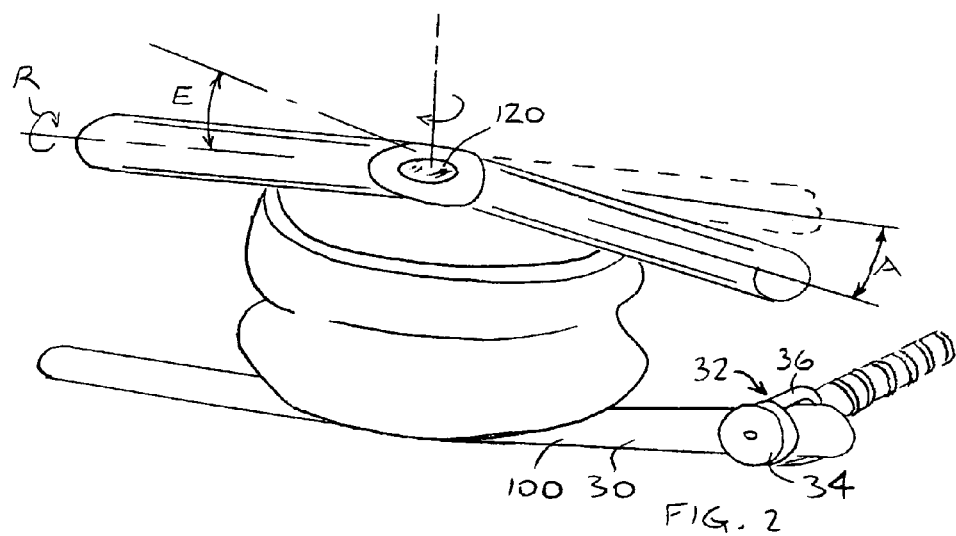
FIG. 2 is a simplified illustration of the spinal prosthesis of FIG. 1, with pedicle screw mounting members moved to different attachment orientations, in accordance with an embodiment of the present invention.

Reference is now made to FIGS. 1 and 2. Pedicle screw mounting members 100 may extend outwards from the first and second spinal prosthetic members 12 and 16. The pedicle screw mounting members 100 may include, but are not limited to, a pair of rounded prongs 30 from which depend pedicle screws 32 (FIG. 2) that screw into spinal structure (e.g., pedicles or spinous processes). As see in FIG. 2, the pedicle screws 32 may include, without limitation, polyaxial pedicle screws, e.g., made of titanium or titanium alloy, commercially available in many sizes and shapes from many manufacturers. It is noted that titanium is highly resistant to corrosion and fatigue, and is MRI compatible. The pedicle screw 32 may have a mobile, swivel head 34, whose ability to swivel may help avoid vertebral stress. The swivel heads 34 may be rotatably attached to the rounded prongs 30 by means of lock nuts 36 that mate with heads 34.

In accordance with an embodiment of the present invention, the pedicle screw mounting member 100 (that is, one or more of them) may be movably attached to the first and second spinal prosthetic members 12 and 16, such that the pedicle screw mounting member 100 has at least two different attachment orientations with respect to reference axes X, Y defined on one of the spinal prosthetic members 12 or 16. For example, as seen in FIG. 1, the pedicle screw mounting member 100 may be pivotable about a pivot 120. The pedicle screw mounting members 100 may be pivotable about a common pivot or each of the pedicle screw mounting member 100 may be pivotable independently of each other about individual pivots. The pivot 120 may permit rotating the pedicle screw mounting member 100 about one rotation axis, or may be a spherical joint that permits rotation about three mutually orthogonal axes. Other pivotal movements are also possible in the invention.

Thus, the pedicle screw mounting member 100 may be pivoted to different attachment orientations that differ from each other by an angular distance about the pivot. For example, without limitation, the pedicle screw mounting member 100 may be pivoted in azimuth as indicated by angle A, or in elevation as indicated by angle E or in roll as indicated by angle R (FIG. 2).

The pedicle screw mounting member 100 may be fixed at a plurality of angles about the pivot 120 (shown in phantom lines in the drawing) such as, without limitation, by "clicking" into place by a ratchet or pawl and detent mechanism. As another example, the spinal prosthetic member 12 and/or 16 may have more than one attachment point 122 for attaching thereto the pedicle screw mounting member 100. In this manner, the pedicle screw mounting member 100 is translatable from one attachment point 122 to another.

Figure 4:
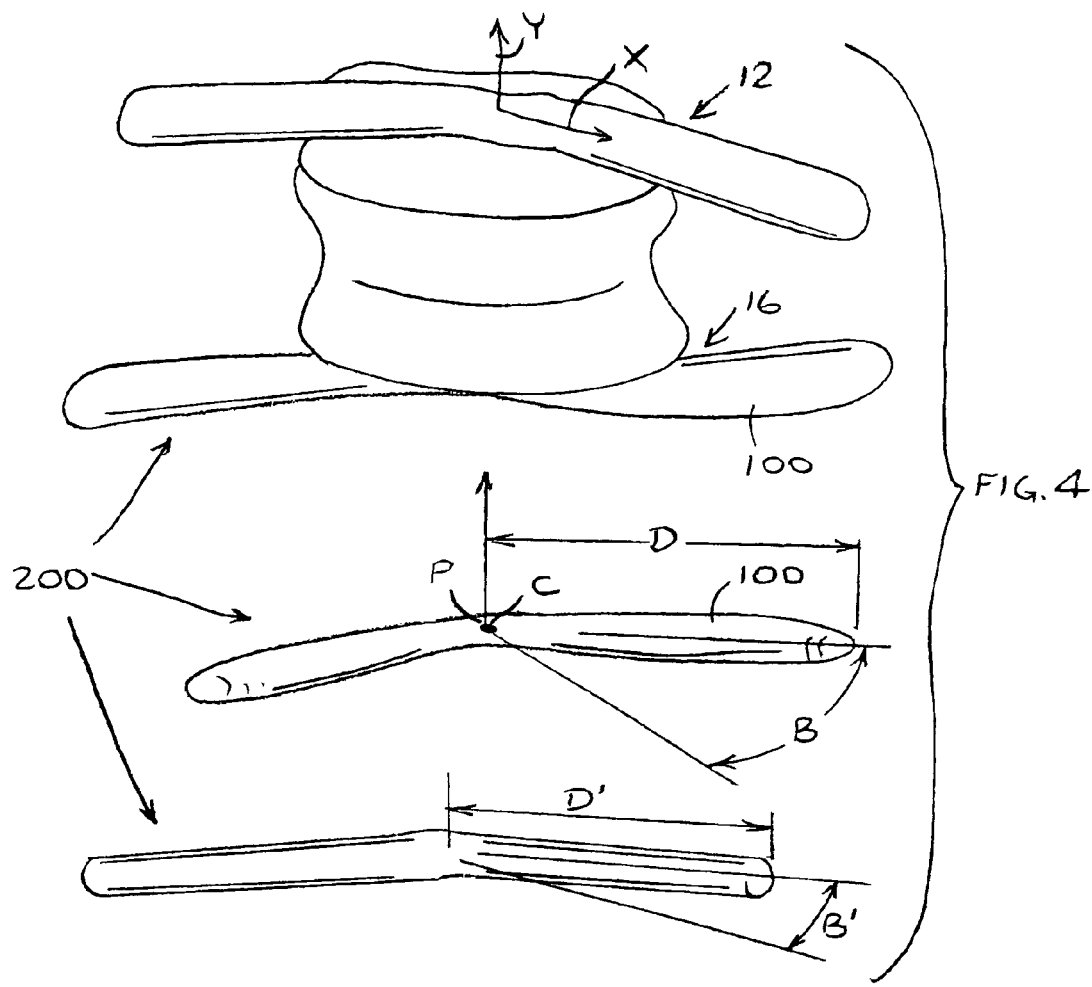
FIG. 4 is a simplified illustration of a kit having a plurality of pedicle screw mounting members, wherein the pedicle screw mounting members have different attachment orientations, constructed and operative in accordance with an embodiment of the present invention.

Reference is now made to FIG. 4. In accordance with another embodiment of the present invention, a kit 200 having a plurality of pedicle screw mounting members 100 may be provided, wherein the pedicle screw mounting members 100 have different attachment orientations with respect to reference axes X, Y defined on one of the spinal prosthetic members 12 or 16. The different attachment orientations may differ from each other by an angular distance B or B' about a reference pivot C. Additionally or alternatively, the different attachment orientations may differ from each other by a linear distance D or D' from a reference point P. The kit may include pedicle screw mounting members 100 of different lengths.

In the prior art, fusion rods may be connected by pedicle screws to spinal structure. Each end of the fusion rod is attached by a pedicle screw to spinal structure. Thus, in the prior art, two or more pedicle screws are attached to some linking rod.

Reference is now made to FIG. 5. In accordance with an embodiment of the present invention, an elongate link element 300 may be connected between one pedicle screw 302 and a non-pedicle-screw structure 304. The elongate link element 300 may include, without limitation, a bar or rod, constructed of materials including, but not limited to, a biocompatible material such as a metal, e.g., stainless steel, titanium or titanium alloy, cobalt chromium alloys, plastics or other hard, rigid materials or any combination of the above.

In one example, the non-pedicle-screw structure 304 may include a portion of a spinal prosthesis 306. In another example, the non-pedicle-screw structure 304 may include a mounting formation 308 formed in a portion of a spinal structure 310. The mounting formation 308 may include, without limitation, a hole or threaded hole formed in the bone, or a mounting post or lug attached to the bone (by threaded fasteners or cement, for example). The pedicle screw 302 and the non-pedicle-screw structure 304 may be positioned at different levels of vertebrae (e.g., one at L5 and the other at S1).

Even though embodiments were described above in which the attachment of attachment members was to either the spinous process alone or to the spinous process and to the facet or to the spinous process and to pedicle of the particular vertebra, it is feasible that any combination of the above embodiments will bring about similar results (such as stabilization of the spine, relief of pain, implantation of the prosthesis, etc.) and the above examples are just examples of attachment sites and not in any way meant to be limiting. For example a superior attachment member may be attached to a spinous process alone and the prosthesis's inferior attachment member may be attached to the adjacent vertebra's spinous process and to its pedicle or facet or even a combination of both. Similarly the prosthesis of this invention may be used in conjunction with an implant that is anterior to the spinal cord such as a total disc replacement.

Although the invention has been described in conjunction with specific embodiments thereof, many alternatives, modifications and variations are apparent to those skilled in the art. Accordingly, all such alternatives, modifications and variations fall within the spirit and scope of the following claims.

What is claimed is:

1. Apparatus comprising:
a first spinal prosthetic member attachable to a first spinal structure;
a second spinal prosthetic member attachable to a second spinal structure and articulating with said first spinal prosthetic member to form an articulating assembly, wherein said articulating assembly comprises a flexure assembly constructed of a compliant, elastomeric material; and
pedicle screw mounting members cantilevered outwards from said first and second spinal prosthetic members, said pedicle screw mounting members being pivotably attached to said first and second spinal prosthetic members about a common pivot such that said pedicle screw mounting members have at least two different attachment orientations with respect to reference axes defined on one of the spinal prosthetic members.

2. The apparatus according to claim 1, wherein said at least two different attachment orientations differ from each other by an angular distance about the common pivot.

3. The apparatus according to claim 2, wherein said pedicle screw mounting members are fixable at a plurality of angles about the common pivot.

4. The apparatus according to claim 1, wherein at least one of the spinal prosthetic members has more than one attachment point for attaching thereto said pedicle screw mounting members, and said pedicle screw mounting members are translatable from one attachment point to another.

5. The apparatus according to claim 1, wherein said pedicle screw mounting members comprises rounded prongs.

6. Apparatus comprising:
a first spinal prosthetic member attachable to a first spinal structure;
a second spinal prosthetic member attachable to a second spinal structure and articulating with said first spinal prosthetic member to form an articulating assembly, wherein said articulating assembly comprises a flexure assembly constructed of a compliant, elastomeric material; and
a kit of pedicle screw mounting members, each pedicle screw mounting member being attachable to as a cantilevered member from at least one of said first and second spinal prosthetic members, the kit comprising a plurality of said pedicle screw mounting members that have different attachment orientations with respect to reference axes defined on one of the spinal prosthetic members, said pedicle screw mounting members being movably pivotably attached to said first and second spinal prosthetic members about a common pivot.

7. The apparatus according to claim 6, wherein said different attachment orientations differ from each other by an angular distance about said common pivot.

8. The apparatus according to claim 6, wherein said different attachment orientations differ from each other by a linear distance from said common point.

9. The apparatus according to claim 6, wherein said kit comprises pedicle screw mounting members of different lengths.

10. The apparatus according to claim 6, wherein said pedicle screw mounting members comprises rounded prongs.

* * * * *